United States Patent [19]

Ichihara

[11] Patent Number: 5,297,035
[45] Date of Patent: Mar. 22, 1994

[54] METHOD AND SYSTEM FOR PROCESSING RI IMAGES IN SPECT APPARATUS

[75] Inventor: Takashi Ichihara, Ootawara, Japan

[73] Assignee: Kabushiki Kaisha Toshiba, Kawasaki, Japan

[21] Appl. No.: 502,238

[22] Filed: Mar. 30, 1990

[30] Foreign Application Priority Data

Apr. 4, 1989 [JP] Japan .................................. 1-84056

[51] Int. Cl.⁵ ........................ G06F 15/00; G01T 1/166
[52] U.S. Cl. .......................... 364/413.13; 250/363.04
[58] Field of Search ................. 364/413.13, 413.14; 250/363.02, 363.04, 363.03; 378/19, 17

[56] References Cited

U.S. PATENT DOCUMENTS

| | | | |
|---|---|---|---|
| 4,086,492 | 4/1978 | Lodge et al. | 250/416 |
| 4,095,107 | 6/1978 | Genna et al. | 250/363.04 |
| 4,117,337 | 9/1978 | Staats | 250/445 |
| 4,216,526 | 8/1980 | Karwowski | 363/414 |
| 4,584,478 | 4/1986 | Genna et al. | 250/363 |
| 4,659,935 | 4/1987 | Hawman | 250/505.1 |
| 4,977,505 | 12/1990 | Pelizzari et al. | 364/413.19 |
| 4,989,142 | 1/1991 | Crawford | 364/413.15 |
| 5,055,687 | 10/1991 | Ichihara | 250/363.04 |
| 5,155,365 | 10/1992 | Cann et al. | 250/363.04 |
| 5,173,608 | 12/1992 | Motomura et al. | 250/363.04 |

Primary Examiner—Roy N. Envall, Jr.
Assistant Examiner—Xuong Chung
Attorney, Agent, or Firm—Oblon, Spivak, McClelland, Maier & Neustadt

[57] ABSTRACT

In a SPECT apparatus, when an OM-line setting line is projected to a subject placed on a top table of a berth apparatus, an OM line is positioned. After the subject is moved to a data acquiring position of a gantry by a berth controller, RI data is acquired. In addition, the position of the OM line is calculated. An RI image is reconstructed by a data processor on the basis of the RI data. The RI image on the OM line can be acquired by performing slice conversion of the reconstructed RI image in accordance with the calculated position of the OM line.

6 Claims, 5 Drawing Sheets

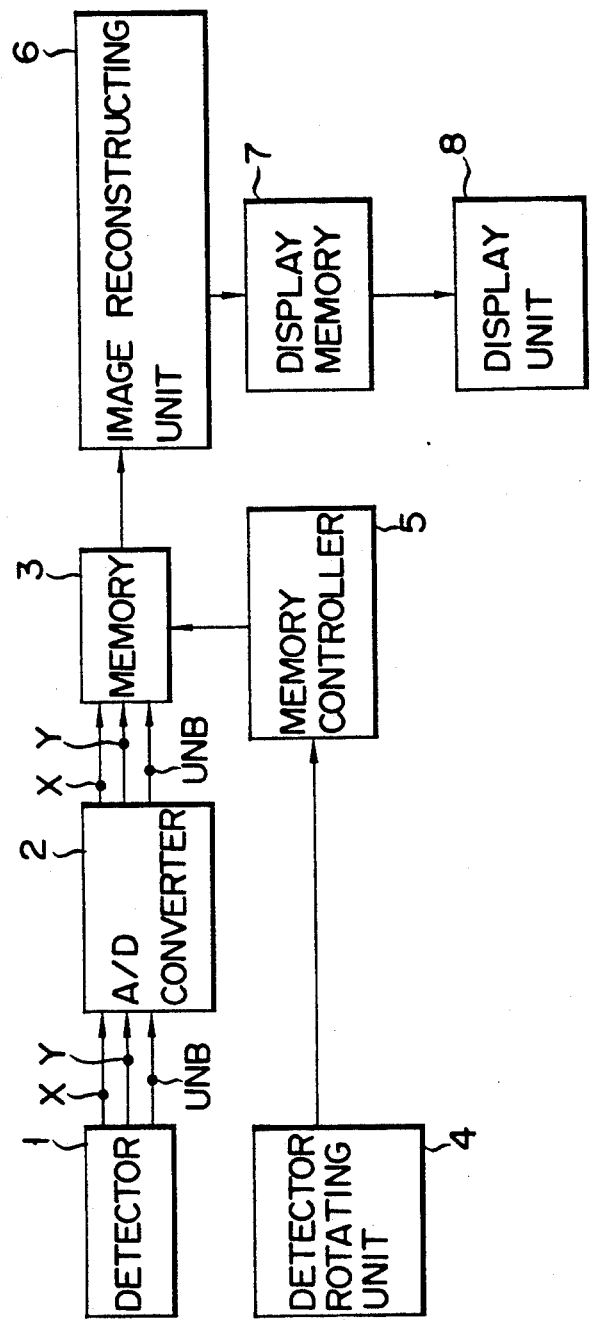
F I G. 1

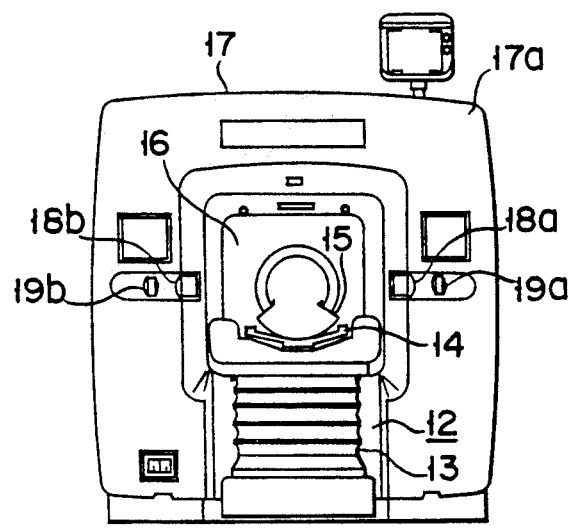
F I G. 4
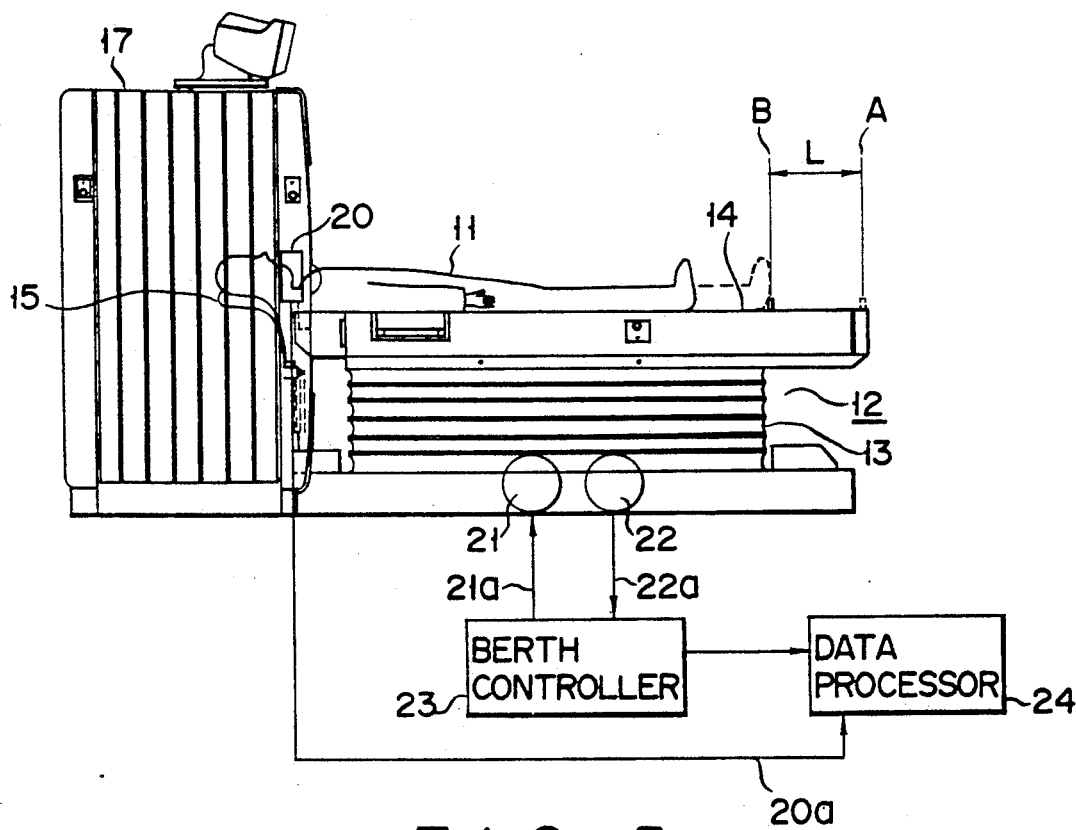
F I G. 5

METHOD AND SYSTEM FOR PROCESSING RI IMAGES IN SPECT APPARATUS

BACKGROUND OF THE INVENTION

1. Field of the Invention

The present invention relates to a method and system for processing RI images in a SPECT apparatus.

2. Description of the Related Art

In a conventional SPECT (single photon emission computed tomography) apparatus shown in FIG. 1, when RI (radioisotope) is injected to a subject to be examined (not shown), radiation from the subject is detected by a detector 1. Position data X and Y and unblank data UNB associated with the radiation detected by the detector 1 are stored in a memory 3 through an A/D converter 2. During detection of radiation, since the detector 1 is rotated about the axis of the subject by a detector rotating unit 4, data detected by the detector 1 at various rotational positions are stored in the memory 3. A rotational position signal representing the rotational position of the detector 1 is output from the detector rotating unit 4 to a memory controller 5. The memory controller 5 causes the memory 3 to output the data stored therein to an image reconstructing unit 6 in response to the rotational position signal. An RI image (SPECT image) is reconstructed by the image reconstructing unit 6 on the basis of the data at each rotational position of the detector 1, and the reconstructed image is displayed on a display unit 8 through a display memory 7.

In the above-mentioned SPECT apparatus, when the subject is placed on a berth so that the axis of the subject substantially coincides with the central axis of rotation of the detector, an RI image 10 to be acquired corresponds to a plane perpendicular to an axis of body 9, as shown in FIG. 2.

As the performance of the SPECT apparatus has been improved in recent years, a case wherein an RI image of a head is acquired for the purpose of diagnosis of the head, e.g., an examination of cerebovascular disease, has, been increased. When RI images are acquired in diagnosis, a head photographing standard line 30 shown in FIG. 3, i.e., a line (to be referred on an OM line hereinafter) which connects an eye to an ear hole of the subject, must be referred to, as in a case wherein an X-ray CT image or an MR (magnetic resonance) image is acquired. In the conventional SPECT apparatus, therefore, the posture of the subject is set so that an OM line is perpendicular to the center of rotation of the detector in order to acquire RI images (slice images) on the OM line.

It is, however, often difficult to set such a posture of a patient which has a trouble in his or her backbone, neck, or the like. In this case, RI images on the OM line cannot be acquired. In order to solve this problem, a SPECT apparatus which can acquire RI images without changing the posture of a patient has been developed. In this SPECT apparatus, the gradient of the OM line is measured in advance by an operator, and the gradient of the OM line is off-line input during image reconstruction processing. According to this apparatus, it is determined that the gradient of an image is equal to that of the OM line. However, it is difficult to specify a tomogram corresponding to the OM line among a plurality of tomograms.

Thus, a demand has arisen for developing a SPECT apparatus which can acquire RI images on a photographing standard line set in a subject regardless of a posture of the subject.

SUMMARY OF THE INVENTION

It is an object of the present invention to provide a method and system for processing RI images in a SPECT apparatus.

According to one aspect of the present invention, there is provided a method for processing RI images in a SPECT apparatus, the method comprising the steps of:

projecting a setting line to the subject;
acquiring RI data of the subject;
calculating a position of the projected setting line;
reconstructing the RI images from the acquired RI data; and
performing coordinates-conversion of the reconstructed RI images in accordance with the calculated position.

According to another aspect of the present invention, there is provided a system for processing RI images in a SPECT apparatus, the system comprising:

projecting means for projecting a setting line to the subject;
acquiring means for acquiring RI data of the subject;
calculating means for calculating a position of the projected setting line;
reconstructing means for reconstructing the RI images from the acquired RI data; and
coordinates-conversion means for performing coordinates-conversion of the reconstructed RI images in accordance with the calculated position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 is a block diagram showing an arrangement of a SPECT apparatus;

FIGS. 4 and 5 are views showing an arrangement of a system according to an embodiment of the present invention;

DETAILED DESCRIPTION OF THE PREFERRED EMBODIMENTS

Figure 2:
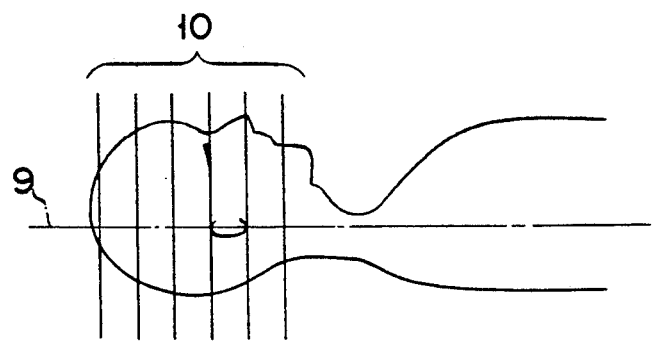
FIG. 2 is a view showing a positional relationship between a subject and RI images.
Figure 3:
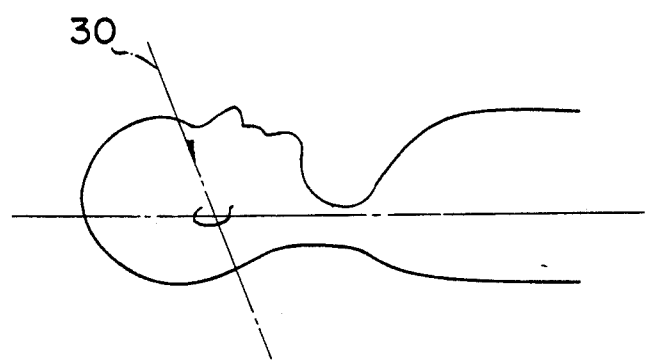
FIG. 3 is a view for explaining a head photographing standard line with respect to the subject.

An embodiment of the present invention will be described hereinafter with reference to the accompanying drawings.

As shown in FIGS. 4 and 5, a system according to the present invention includes a berth apparatus 12, a gantry 17, a berth controller 23, and a data processor 24.

The berth apparatus 12 includes a vertically moving mechanism 13, a top table 14, a berth drive section 21, and a position sensor 22. The top table 14 is mounted on the vertically moving mechanism 13. The berth drive section 21 vertically moves the vertically moving mechanism 13 to move the top table 14 in the axial direction of the subject. The position sensor 22 detects the movement position of the top table 14, and outputs a position signal 22a representing the detected movement position to the berth controller 23.

The berth controller 23 outputs a drive signal 21a to the berth drive section 21 in response to the position signal 22a from the position sensor 22 to drive the berth drive section 21. In addition, the position signal 22a is input to the data.

Figure 6:
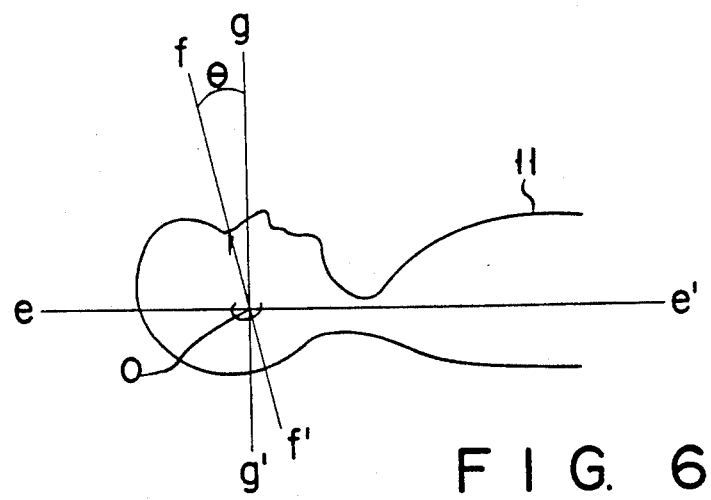
FIG. 6 is a view showing horizontal and vertical project lines and an OM-line setting line projected to the subject by a projector.

The gantry 17 includes a headrest 15, an opening 16 in which a subject 11 is arranged, a projector 18a, and a projector rotating section 19a. Note that a projector 18b and a projector rotating section 19b can be arranged, if necessary. The headrest 15 is used to hold the head of the subject 11. A one- or two-dimensional radiation detector (not shown) which rotates around the subject 11 is arranged in the gantry 17. The projector 18a is arranged near the opening 16 on a surface 17a of the gantry 17. As shown in FIG. 6, the projector 18a projects horizontal and vertical project lines e—e' and g—g', and an OM-line setting line f—f' to the subject 11. The OM-line setting line f—f' is rotated by the projector rotating section 19a. An encoder 20 detects a rotational angle of the OM-line setting line f—f' to output a rotational angle signal 20a representing the detected rotational angle to the data processor 24.

Figure 7:
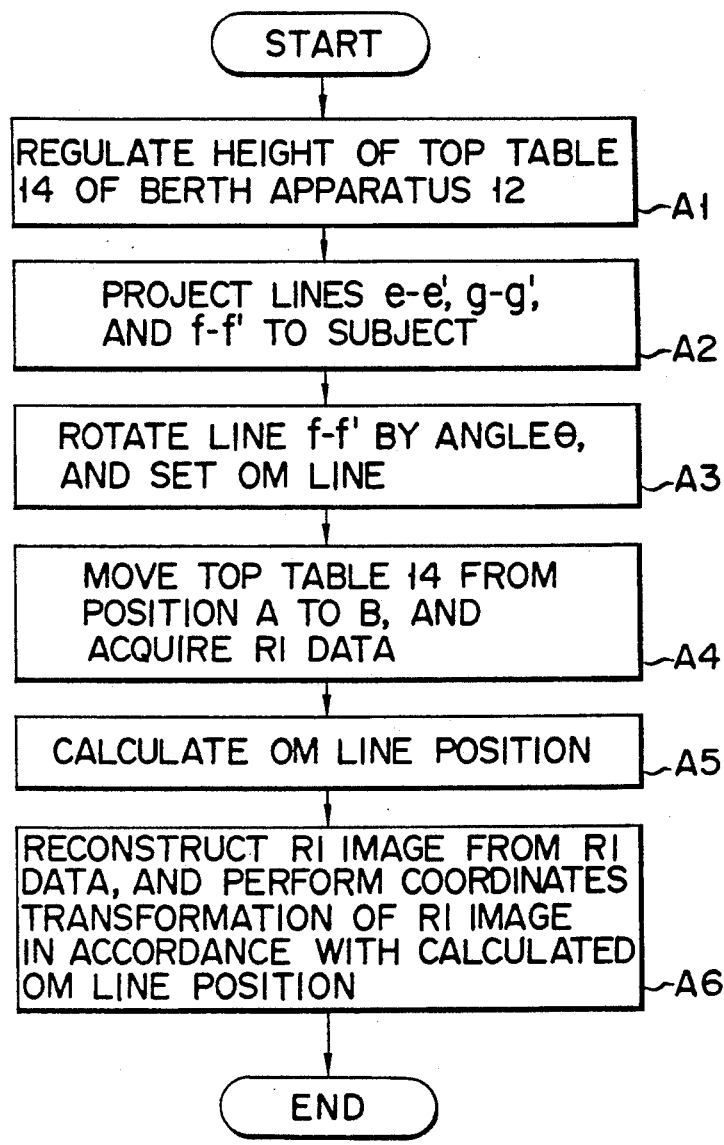
FIG. 7 is a flow chart for explaining acquisition of RI images according to the system of the present invention.

An operation of this system will be described hereinafter following a flow chart in FIG. 7.

In step A1, when the vertically moving mechanism 13 is driven, the height of the top table 14 of the berth apparatus 12 on which the subject 11 is placed is regulated. Therefore, the head of the subject 11 is optimally positioned with respect to the projector 18a.

In step A2, when the projector 18a is driven, the horizontal and vertical project lines e—e' and g—g', and the OM-line setting line f—f' are projected to the subject 11, as shown in FIG. 6. Note that an intersecting point of the lines e—e', g—g', and f—f' coincides with the position of the ear hole of the subject 11.

In step A3, the OM-line setting line f—f' is rotated by a rotational angle $\theta$ by the projector rotating section 19a so that the OM-line setting line f—f' coincides with a line which connects the position O of the ear hole to the position of the eye in the subject 11, i.e., an OM line. After the OM line is set, a rotational angle signal representing the rotational angle $\theta$ detected by the encoder 20 is input to the data processor 24.

In step A4, in order to acquire RI data corresponding to the head of the subject 11, the top table 14 is moved from a position A to a position B by a moving amount L, as shown in FIG. 5. Note that FIG. 5 shows the position of the top table 14 after movement.

Figure 8:
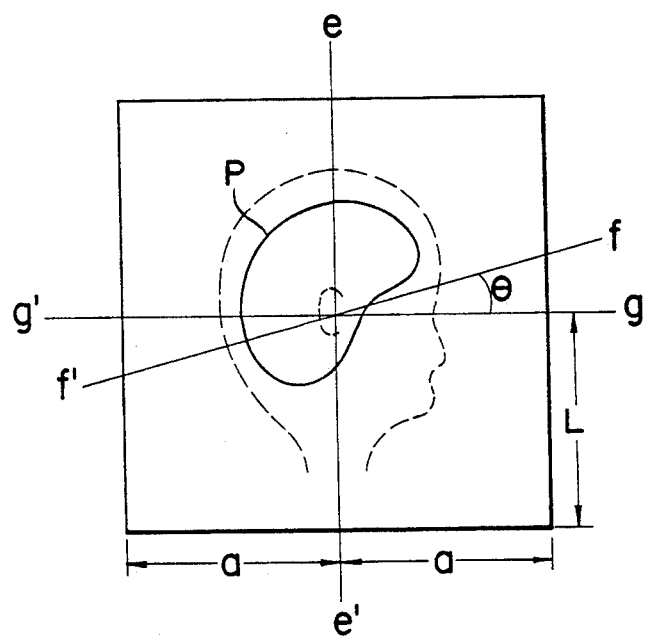
FIG. 8 is a view showing a positional relationship between an RI image of the subject and the OM-line setting line.

In step A5, as shown in FIG. 8, in accordance with the positional relationship between a head RI image P of the subject 11 and the OM line f—f' in consideration of the moving amount L, a line rotated from the vertical line g—g' by the rotational angle $\theta$ centered on a and L serves an actual OM line. Such calculation processing is performed by the data processor 24. The calculated position data representing the position of the OM line is stored in a memory (not shown) of the data processor 24 together with the RI data.

Figure 9:
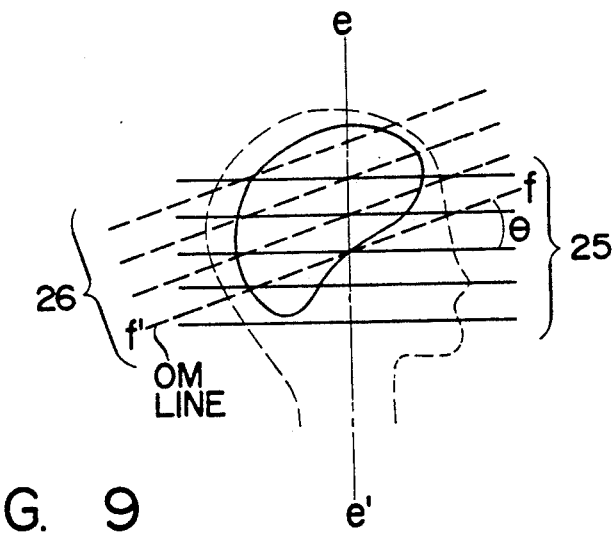
FIG. 9 is a view for explaining acquisition of RI images on an OM line.

In step A6, as shown in FIG. 9, RI images 25 which are perpendicular to the axis e—e' of the subject 11 are reconstructed on the basis of the RI data. The reconstructed RI images 25 are converted into RI images 26 by the angle $\theta$ formed by the OM line in accordance with the position data of the OM line to perform coordinates conversion of RI images. The converted RI images 26 include the RI images on the OM line. Note that when the RI images 26 are separated from the OM line, the RI image can be easily compared with, e.g., an X-ray CT image.

Although a case wherein the intersecting point 0 of the OM-line setting line f—f' and other project lines coincides with the ear hole of a human body has been described in the above embodiment, the present invention is not limited thereto.

Additional advantages and modifications will readily occur to those skilled in the art. Therefore, the invention in its broader aspects is not limited to the specific details, representative devices, and illustrated examples shown and described herein. Accordingly, various modifications may by without departing from the spirit or scope of the general inventive concept as defined by the appended claims and their equivalents.

What is claimed is:

1. A method for processing RI (radioisotope) images of a subject in a SPECT (single photon emission computed tomography) apparatus, comprising the steps of:
   setting an angle of a visible line, said visible line being a line of light projected to an axis of the subject;
   acquiring RI data of the subject using a detector rotatably around said axis of the subject;
   reconstructing a plurality of RI images perpendicular to said axis of the subject; and
   preforming coordinates conversion of said RI images in accordance with said angle of the visible line, to obtain RI images parallel to said visible line.

2. The method according to claim 1, wherein the setting step includes the step of fitting the visible line to a standard line which is representative of a line joining a position of an eye to a position of an ear hole in the subject.

3. The method according to claim 2, wherein one of said RI images corresponds to an RI image concerning the standard line.

4. A system for processing RI (radioisotope) images of a subject in a SPECT (single photon emission computed tomography) apparatus, comprising the steps of:
   setting means for setting an angle of a visible one projected to an axis of the subject;
   a detectable rotatably around said axis of the subject;
   acquiring means for acquiring RI data of the subject using the detector;
   reconstructing means for reconstructing a plurality of RI images perpendicular to said axis of the subject; and
   coordinates-conversion means for performing coordinates conversion of said RI images in accordance with said angle of the visible line, to obtain RI images parallel to said visible line.

5. The system according to claim 4, wherein the setting means includes means for fitting the visible line to a standard line which is representative of a line joining a position of an eye to a position of an earhole in the subject.

6. The system according to claim 5, wherein one of said RI images corresponds to an RI image concerning the standard line.

* * * * *